United States Patent [19]

Trentacosta

[11] Patent Number: 5,397,365
[45] Date of Patent: Mar. 14, 1995

[54] COMPOSITE ORTHOPEDIC IMPLANT WITH MODULUS VARIATIONS

[75] Inventor: Joseph D. Trentacosta, Wilmington, Del.

[73] Assignee: E. I. Du Pont de Nemours and Company, Wilmington, Del.

[21] Appl. No.: 71,626

[22] Filed: Jun. 3, 1993

Related U.S. Application Data

[63] Continuation of Ser. No. 823,081, Jan. 14, 1992, abandoned, which is a continuation of Ser. No. 531,651, Jun. 1, 1990, abandoned.

[51] Int. Cl.$^6$ .............................................. A61F 2/30
[52] U.S. Cl. ....................................... 623/18; 623/16; 623/22; 623/23; 606/76
[58] Field of Search ................... 623/16, 18, 22, 23; 606/76, 77, 78

[56] References Cited

U.S. PATENT DOCUMENTS

| | | | |
|---|---|---|---|
| 4,280,233 | 7/1981 | Raab | 3/1.91 |
| 4,301,551 | 11/1981 | Dore et al. | 623/1 |
| 4,408,359 | 10/1983 | Burstein | 623/16 |
| 4,662,887 | 5/1987 | Turner et al. | 623/16 |
| 4,728,335 | 3/1988 | Jurgutis | 623/23 |
| 4,750,905 | 6/1988 | Koeneman et al. | 623/16 |
| 4,892,552 | 1/1990 | Ainsworth et al. | 623/23 |
| 4,986,834 | 1/1991 | Smith et al. | 623/23 |
| 4,997,444 | 3/1991 | Farling | 623/16 |
| 5,064,439 | 11/1991 | Chang et al. | 623/66 |
| 5,314,492 | 5/1994 | Hamilton et al. | 623/16 |

FOREIGN PATENT DOCUMENTS

| | | |
|---|---|---|
| 19044 | 11/1980 | European Pat. Off. |
| 0277727 | 8/1988 | European Pat. Off. |
| 8504323 | 10/1985 | WIPO |
| 8704916 | 8/1987 | WIPO |

OTHER PUBLICATIONS

O'Neil, David A., Cornell University, 1989, *Design and Analysis of Composite Total Hip Replacemennt Stems.*

*Primary Examiner*—Paul Prebilic

[57] ABSTRACT

Novel composite orthopedic devices with modulus variations are disclosed. The device contains an extraosseous portion attached to a first intraosseous portion which is secured to a second intraosseous portion; the intraosseous portions may interface with the intramedullary canal of the human femur. The modulus varies along the length of the device, decreasing from the extraosseous portion to the second intraosseous portion. The variations in modulus are achieved by forming the device from a composite comprising filaments nonlinearly disposed about the longitudinal axes of the device and within a polymer matrix. The method of making the present orthopedic device is also disclosed.

13 Claims, 4 Drawing Sheets

COMPOSITE ORTHOPEDIC IMPLANT WITH MODULUS VARIATIONS

This is a continuation of application Ser. No. 07/823,081, filed Jan. 14, 1992, abandoned, which is a continuation of Ser. No. 07/531,651, filed Jun. 1, 1990.

FIELD OF THE INVENTION

The present invention relates to orthopedic implants, and more particularly to load bearing prosthetic devices that exhibit along the length modulus variations, and methods of preparation thereof.

BACKGROUND OF THE INVENTION

Orthopedic implants include a wide variety of devices, each suited to fulfill particular medical needs. Examples of such devices are hip joint replacement devices, knee joint replacement devices, and pins, braces and plates used to set fractured bones. Particular emphasis has been recently placed on hip joint prosthetic equipment.

Contemporary orthopedic implants, including hip and knee components, use high performance metals such as cobalt-chrome and titanium alloy to achieve high strength. These materials are readily fabricated into the complex shapes typical of these devices using mature metal working techniques including casting and machining. Yet, these metals are characterized by high, fixed moduli of elasticities which makes it difficult to achieve optimal device stiffness within a given anatomical geometric envelope. In particular, in regions in which metal implants share load with surrounding bone, e.g., the medullary canal of the femur, the stress in the bone is substantially reduced versus the normal physiological level. This "stress-shielding" effect often leads to bone remodeling and may be implicated in clinical problems such as aseptic loosening and pain. Stress shielding is particularly acute in large metal implant systems. Further, large metal implants require more bone cement and are more susceptible to loosening than smaller implants.

Since metals are characterized by a single, high modulus of elasticity (16 million psi for titanium alloy and 31 million psi for cobalt-chrome alloy) it is apparent that optimal design of metallic devices must focus on the geometric part of the rigidity without regard to the material parameter. Geometric design has several constraints. For example, it is generally agreed that good bone apposition is necessary for bone ingrowth into proximal porous coatings and that close distal stem fit is necessary for rotatory stability.

Composite materials offer the potential to achieve high strength in orthopedic devices while permitting the control of stiffness for enhanced load transfer to bone. In particular, the implant designer can control modulus by varying reinforcement type, orientation and amount. Such a device is revealed in PCT patent application WO/85/04323. The device is formed from a composite material of continuous filament carbon fibers embedded within a polymer matrix. The carbon fibers in the composite material are at specific orientations relative to a specific dimension of the orthopedic device. The angularity of the carbon fibers modifies the modulus of the device. To effect fiber orientation, uniplanar sheets of carbon fibers are formed and cut into coupons. The coupons are then stacked into blocks or rolled into cylinders, to be fashioned into the final device. The manner in which the sheets or coupons are oriented will affect final mechanical properties. However, this device is limited in that the orientation of the carbon fibers cannot be systematically varied along the formed elongated body.

European Patent Publication 0277 727 discloses an orthopedic device of a biocompatible polymer with oriented fiber reinforcement. Prostheses of this reference are formed from plies of continuous filament fibers that are curvilinearly disposed within a body. The plies may have a balanced orientation; that is, for each sheet having fibers offset at a positive angle there is essentially a sheet having fibers offset at about the same negative angle. However, the prosthetic device of this variety is limited in that the orientation of the carbon fibers cannot be varied along the formed elongate body.

U.S. Pat. No. 4,750,905 reveals a prosthesis construction including an elongate, tapered polymer core containing continuous-filament fibers oriented substantially along the length of the core. The core includes an elongate distal stem. A braided sheath encases the stem. The filaments in the braid encircle the core in a helical pattern. However, devices according to this reference cannot be formed in a flexible laydown pattern as in the present invention.

It is an object of the present invention to provide an orthopedic implant with variable modulus wherein the stresses in the surrounding bone are more nearly equal to their normal physiological level than achieved in a system without modulus variations. It is a feature of the present invention to provide a variety of composite materials to design an orthopedic implant with particular properties. It is an advantage of the present invention that the subject orthopedic implants have a variable modulus along their lengths due to the use of filament winding and braiding techniques.

These and other objects, features and advantages of the present invention will become more readily apparent with reference to the following description of the invention.

SUMMARY OF THE INVENTION

The present invention provides an orthopedic device for human implantation comprising an extraosseous portion, a first intraosseous portion attached thereto and a second intraosseous portion attached to said first intraosseous portion. The orthopedic device is made of composite material, with the extraosseous portion having a modulus greater than the modulus of the second intraosseous portion.

In another embodiment according to the invention, the modulus of the first intraosseous portion is greater than the second intraosseous portion and less than the modulus of the extraosseous portion. In general, the modulus of the orthopedic device may vary along the length thereof. This includes continuous variation; different regions having particular moduli, and combinations thereof.

The modulus variation may be accomplished according to another embodiment of the invention, wherein the orthopedic device is made of composite material comprising a plurality of filaments disposed within a polymer matrix. The filaments may be linearly or non-linearly disposed about the longitudinal axes of the extraosseous portion and the first and second intraosseous portions. The filaments may also be disposed in either a helical or a braided pattern, and further other filaments may be incorporated therein oriented axially along the longitudinal axes of the extraosseous portion and the first intraosseous portion.

The orthopedic device of the invention may be prepared according to a process of the invention. The process comprises shaping a mandrel in the configuration of the device, and winding or braiding filaments around the mandrel and applying a polymer matrix to form a layer. Additional layers may be disposed independently about the various portions thereof. The mandrel may be removed.

DETAILED DESCRIPTION OF THE INVENTION

The orthopedic devices of this invention are considered to have a wide range of applicability throughout the human body. Thus, the extraosseous and intraosseous portions relate generally to any portion of the body where they may be implanted into bone and further where prosthetics are desirable. For example, the devices may be implanted to support rotational movement at the shoulder, knee, hip, and the like. Much attention is focused herein on the relation of the orthopedic device to a hip implant. For this use, the extraosseous portion is considered a neck, the first intraosseous portion is considered a proximal body and the second intraosseous portion is a distal stem. While many of the features of the invention are discussed in the context of a hip implant system, it is intended that the many components of the invention be given the wider applicability to implants throughout the body.

Figure 1:
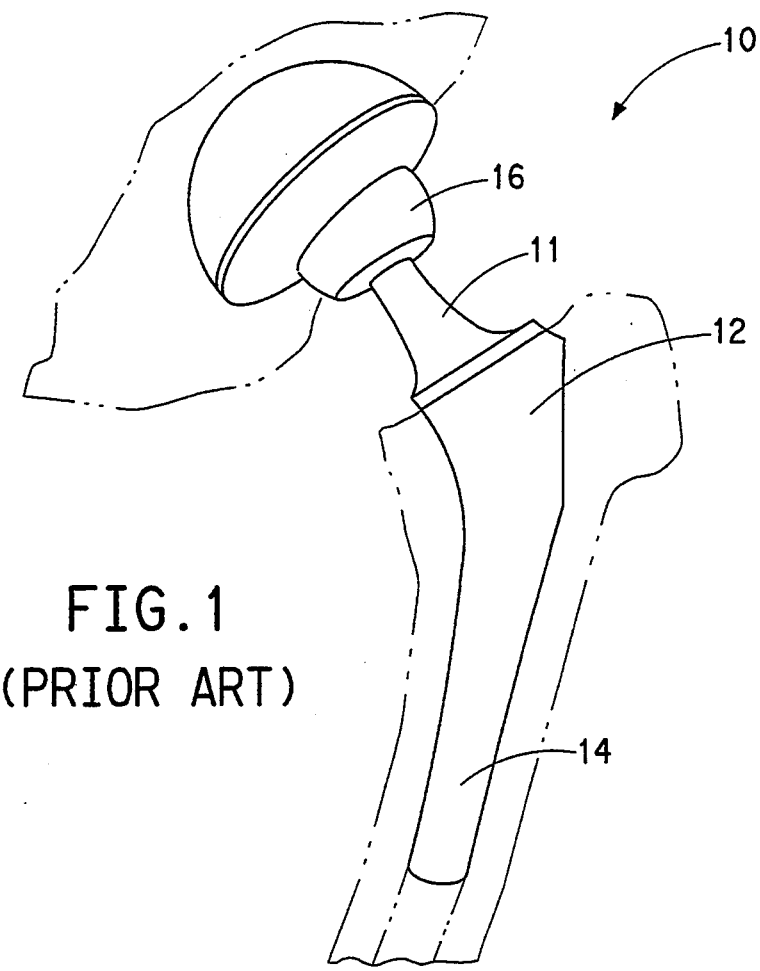
FIG. 1 is a side view of a typical hip implant.

Having reference to FIG. 1, a basic design of a hip implant is illustrated at 10. A neck 11 is secured to proximal body 12 which in turn is attached to a distal stem 14. The neck 11 engages a ball 16, which is rotatably engaged within an artificial cup attached to the pelvis. The proximal body 12 and distal stem 14 are positioned within an orifice in the femoral canal.

Note that the neck 11 of the femoral component is not surrounded by bone—the natural femoral neck is removed in conventional hip surgery along with the natural head. As such, the prosthetic neck 11 must bear the resultant loads and moments transmitted to the femur from the joint and surrounding muscles without load sharing. So, the neck 11 must be adequately strong to avoid structural failure and adequately stiff to avoid excessive deflections which would compromise joint kinematics. There are constraints on the diameter of the neck region imposed by the need to maintain adequate range of motion of the joint.

The proximal body 12 of the femoral component provides the primary interface of the prosthesis with the femur in the trochanteric region. The proximal body 12 is designed for a tight interference fit (or, 'press fit') to the proximal femur. Such a fitting is assisted by the ingrowth of bioactive surfaces. Ideally, the proximal body 12 is given an anatomical shape to follow the contours of the intramedullary canal of the natural femur, thus, minimizing the removal of natural bone and maximizing the structural capacity of the compound bone-implant system. Alternatively, the proximal body 12 is undersized to permit grouting with polymethylmethacrylate (PMMA) bone cement.

The distal stem 14 serves to provide a secondary interface of the device to bone and, in particular, resist rotatory or 'toggling' motions which might compromise proximal fixation and long term biological fixation. The distal stem 14 may be press fit (attempting to follow the natural anatomy) or undersized and grouted with PMMA.

For each functional zone of the device (neck, proximal body and distal stem) one can define a set of rigidities and strengths which characterize the mechanical response of that region. Generally, the rigidities comprise the product of two quantities: a geometric parameter and a material parameter. In particular, we can define three rigidities as follows:

Axial Rigidity=Area X Modulus
Flexural Rigidity=Moment-of-Inertia X Modulus
Torsional Rigidity=Polar Moment-of-Inertia X Shear Modulus It is these rigidities which determine the response of the system to imposed loads and, in particular, control the extent to which the device shares load with any surrounding bone. Generally, load transfer will increase as device rigidity is reduced. Devices which maximize the amount of load transfer to surrounding bone are to be preferred since they will result in reduced bone remodeling consequent to "stress shielding".

However, regional rigidities must be high enough to achieve the functional requirements of the device. As noted above, the neck 11 must be stiff enough to minimize deflections which would otherwise destroy the proper kinematics of the joint. The distal stem 14 must have adequate flexural rigidity to resist 'rocking' or 'toggling' instability. In the present invention the distal stem is designed to optimize rigidity to meet the competing requirements of load transfer and rotatory stability. In addition, regional properties must be adequate to avoid structural failure of the device. Material strength usually correlates with material modulus which, thus, also sets constraints on the degree to which rigidity can be reduced to enhance load transfer.

Orthopedic implants of composite materials including fibers embedded within a polymer matrix offer the ability to control modulus of the implant by selectively orienting the fiber patterns with respect to the longitudinal or load axis of the device. In one composite system wherein a hip implant as in FIG. 1 was constructed of AS4 graphite fibers within a polyether-ether-ketone matrix, the modulus of the implant was computed as the angle of the fibers formed relative of the load axis was allowed to vary. A tenfold variation in modulus is observed by varying the fiber orientation from 0° to 75° from the load axis. In particular, the use of axially oriented fibers (considered 0°–5° offset from the load axis) markedly increases modulus of the implant. Note further that for this system a fiber orientation of from 0° to 75° corresponds to a modulus range of about 1 million to about 19 million psi. The modulus of cortical bone (2.5 million psi) as well as the modulus of titanium-/aluminum/vanadium alloy (16 million psi) are included within this range. In composite systems offering more than a single orientation of fiber, it is apparent that increasing the amounts of axially oriented fibers will increase the modulus. Variations in modulus can also be effected by changing fiber type (e.g., aramid v. graphite) and fiber concentration.

In selecting the percentages of fibers of particular orientations for a given composite system, one skilled in the art also examines the strength response of the system as a function of fiber orientation. Thus, in the system developed previously with graphite fibers in polyether-ether-ketone polymer matrix, a system with 100% axial fiber orientation exhibited a compressive strength of 160 ksi. A similar system containing 60% axial fiber orientation and 40% fiber orientation varied from 5° to 75° exhibited a varied compressive strength from about 150 to about 70 ksi. It is important to note that compressive strength generally (but not necessarily) decreases as the percentage of axial fiber orientation decreases or as the load angle of the nonaxial fiber increases For a desired composite system composite strength must be measured by the designer relative to fiber orientation. However, it is clear that for regions of a device where high strength is prerequisite (e.g., the neck of a typical hip implant) low angle constructions are required relative to the directions of principal stress.

The present invention is directed to orthopedic implants, made from advanced composite materials and having an intentional variation in modulus along the length of the device. In particular, a femoral component for a hip implant is defined which has high modulus in the proximal region (the neck and it's vicinity) and a lower modulus in the distal stem region. Specifically, the neck region has a modulus equal to or higher than typical metal alloys used in current orthopedic devices. This insures that the neck region does not undergo excessive deflections which would compromise functionality of the joint. The distal stem region comprises a modulus which optimizes load transfer to surrounding bone and rotatory stability of the structure. In particular, a preferred range for the modulus in the distal stem is 1 million to 8 million psi. The most preferred modulus will vary with the geometry of the system (e.g., the stem diameter).

Detailed design of the second intraosseous portion can be based on an analysis of the mechanical loading conditions in this portion and the surrounding bone. It is an objective of the present invention to enhance load transfer to the surrounding bone by using a composite vs. a metal distal stem. In particular, the present invention achieves a stress level in the bone closer to the normal physiological level than achieved with conventional all-metal implants.

Figure 3:
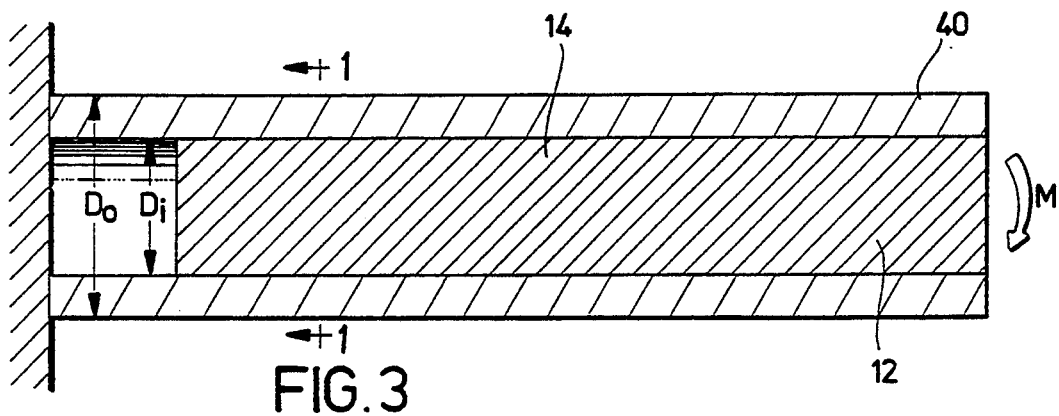
FIG. 3 is a mechanical idealization of a composite hip implant.
Figure 4:
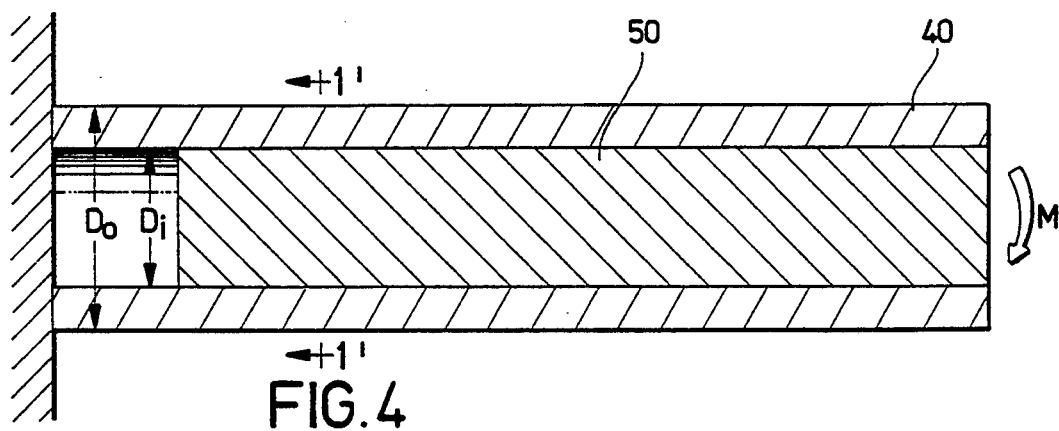
FIG. 4 is a mechanical idealization of a press fit metal hip implant.
Figure 5:
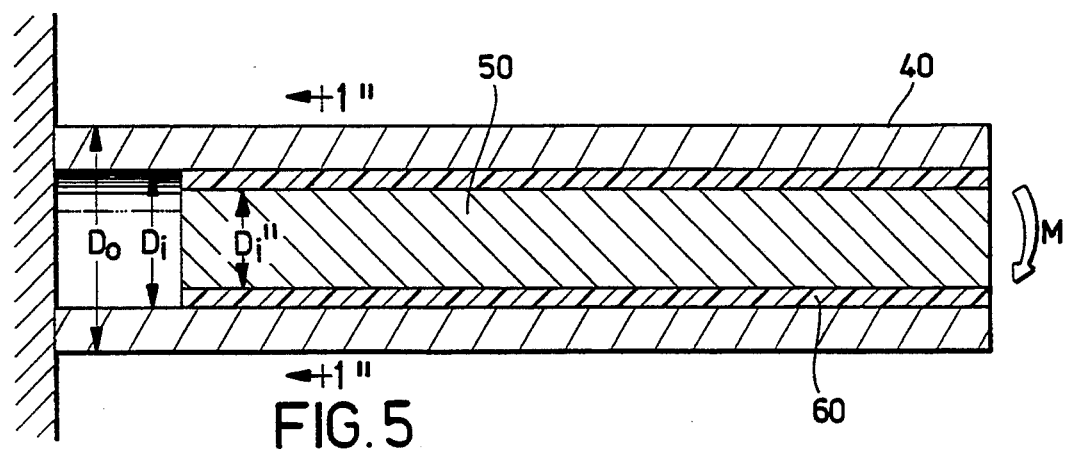
FIG. 5 is a mechanical idealization of a polymethylmethacrylate grouted hip implant.

FIG. 3 shows a mechanical idealization of a hip implant according to the invention in which distal composite stem 14 and proximal body 12 are modeled as cylindrical entities fixed within a hollow cylinder of bone 40 representative of the shaft of the femur. Note that regions 12 and 14 need not have the same modulus of elasticity. For comparison, FIG. 4 shows an analogous idealization for an all-metal system 50 press fit into bone 40 and FIG. 5 is of an analogous idealization for an all-metal system 50 grouted into bone 40 using polymethylmethacrylate bone cement 60. In all three figures the idealized structure is subjected to bending moment M; bending being the principle mode of loading of hip implant systems.

The following nomenclature is used throughout this discussion:

$D_o$: outer diameter of bone 40
$D_i$: inner diameter of bone 40, and, outer diameter of distal portion of stem 14, and, outer diameter of stem 50
$D_i''$: outer diameter of PMMA grouted stem 50
$I_b$: moment of inertia of bone cross section 40
$I_c$: moment of inertia of distal portion of composite stem 14
$I_{c2}$: moment of inertia of proximal portion of composite stem 12
$I_m'$: moment of inertia of press fit stem 50 $I_m''$: moment of inertia of PMMA grouted stem 50 $I_p$: moment of inertia of PMMA cross section $E_b$: modulus of elasticity of bone 40 $E_c$: modulus of elasticity of distal portion of composite stem 14
$E_{c2}$: modulus of elasticity of proximal portion of composite stem 12
$E_m$: modulus of elasticity of metal
$E_p$: modulus of elasticity of PMMA
$L_1, L_2, L_3, L_4$: lengths in figures The maximum bending stress in bone 40 at section 1—1 for the system shown in FIG. 3 is found using mechanics of materials analysis to be $$\sigma_b = \frac{M E_b D_o/2}{E_b I_b + E_c I_c}$$

This can be compared to the maximum bending stress in the bone without the implant in place $$\sigma_{bo} = \frac{M D_o/2}{I_b}$$

It is an objective of the current invention to maximize the ratio $\sigma_b/\sigma_{bo}$ by modification of the modulus of elasticity of the composite, $E_c$.

For comparison, the maximum bending stress in bone 40 at section 1'—1' for the press fit metal system of FIG. 4 is $$\sigma_b' = \frac{M E_b D_o/2}{E_b I_b + E_m I_m'}$$

and the maximum bending stress in bone 40 at section 1''—1'' for the PMMA grouted system of FIG. 5 is $$\sigma_b'' = \frac{M E_b D_o/2}{E_b I_b + E_m I_m'' + E_p I_p}$$

By forming the ratios $\sigma_b/\sigma_b'$ and $\sigma_b/\sigma_b''$ one can quantify the improvement in load transfer with a composite stem vs. the press fit metal stem and PMMA grouted metal stem. In particular, it is an objective of the current invention that the modulus of the distal composite stem be selected such that these ratios are both greater than 1 signifying that the stress in the bone is greater than that achieved for either the press fit metal stem or the PMMA grouted metal stem. To better define this criteria we consider the following typical values for the parameters defining the mechanical idealizations:

$D_o$=25 to 35 (mm) Bone outer diameter
$D_i$=12 to 22 (mm) Bone inner diameter and Composite stem and Press fit Metal stem diameter
$D_i''=(D_i- 4)$ (mm) Grouted metal stem diameter
$E_b$=2.5 million psi
$E_m$=16 million psi for Ti-6Al-4V alloy
$E_p$=0.33 million psi The ratio $\sigma_b/\sigma_b'$ was computed as a function of composite modulus up to 16 million psi for each of two bone outer diameters. For all values of $E_c$ less than the modulus of the metal stem, the ratio $\sigma_b/b''$ is greater than 1; i.e., the bone stress is always higher in the composite implant system than in the press fit metal system if $E_c<E_m$. Thus, the modulus of a low modulus metal, titanium alloy, is one upper limit for the composite modulus of the invention.

The ratio $\sigma_b/\sigma_b''$ was computed as a function of composite modulus up to a value of 16 million psi. It is apparent that for each stem diameter there is a modulus $E_1$ lower than the modulus of the metal at which the ratio $\sigma_b/\sigma_b''$ becomes equal to one. At values of composite modulus lower than $E_1$ the ratio $\sigma_b/\sigma_b''$ is greater than 1. This value of modulus, thus, becomes a more preferred upper limit for the modulus of the composite stem. We state this criteria is $$E_c<E_1 \text{ where } \sigma_b/\sigma_b''=1 \text{ when } E_c=E_1.$$

Figure 6:
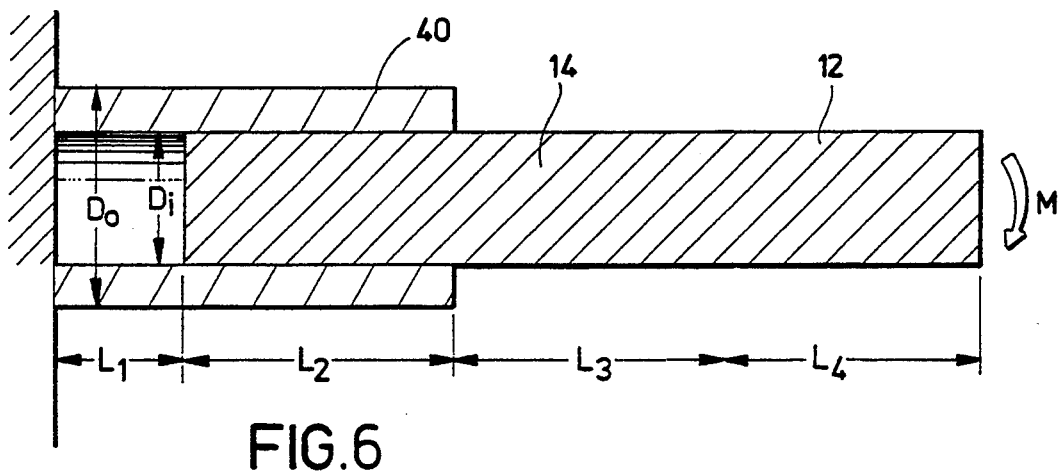
FIG. 6 is another mechanical idealization of a composite hip implant.

Those skilled in the art will recognize that there are other constraints on a hip implant system which may limit the maximum value of $\sigma_b/\sigma_{bo}$ which can be attained in practice. The stem must, for example, be stiff enough to resist rotatory motion if proximal bone support is lost as modeled in FIG. 6. The distal stem 14 remains well fixed to bone 40 but the proximal region 12 no longer makes intimate contact with bone. Physiologically, this lack of proximal bone support may typify the immediate post operative period prior to tissue ingrowth into proximal porous fixation means or be representative of the state of the implant years after implantation where bone remodeling has caused loss of bone support. In either case the distal stem 14 must have sufficient rigidity to resist rotatory motion caused by moment M. The rotatory stiffness of the structure in FIG. 6 is given by:

$$S = \frac{1}{\left[\frac{L_1}{E_b I_b} + \frac{L_2}{E_b I_b + E_c I_c} + \frac{L_3}{E_c I_c} + \frac{L_4}{E_{c2} I_{c2}}\right]}$$

Figure 7:
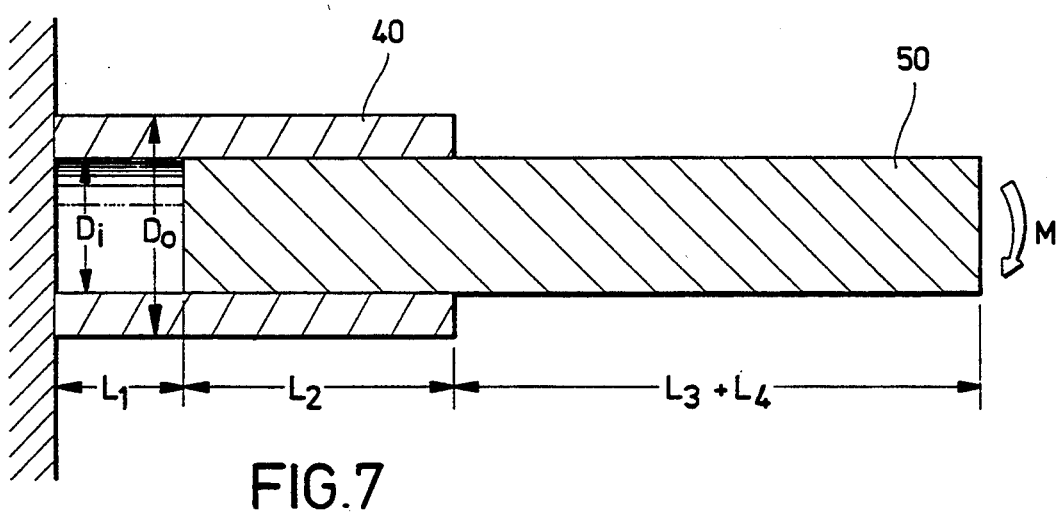
FIG. 7 is another mechanical idealization of a press fit metal hip implant.
Figure 8:
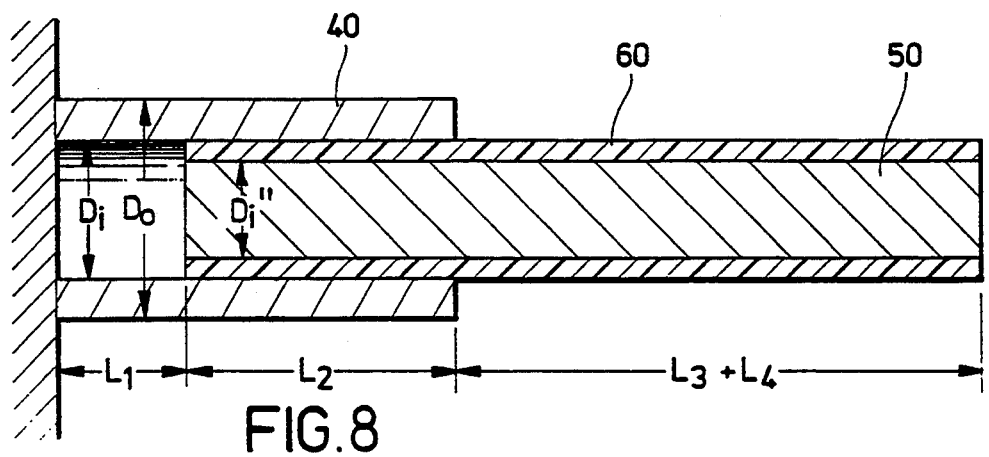
FIG. 8 is another mechanical idealization of a polymethylmethacrylate grouted hip implant.

Again, for comparison FIGS. 7 and 8 present idealized mechanical models for rotatory stiffness for a press-fit all metal system and a PMMA grouted system respectively. The rotatory stiffness for these structures are given respectively as:

$$S' = \frac{1}{\left[\frac{L_1}{E_b I_b} + \frac{L_2}{E_b I_b + E_m I_m'} + \frac{L_3 + L_4}{E_m I_m'}\right]}$$

$$S'' = \frac{1}{\left[\frac{L_1}{E_b I_b} + \frac{L_2}{E_b I_b + E_m I_m'' + E_p I_p} + \frac{L_3 + L_4}{E_m I_m'' + E_p I_p}\right]}$$

It is apparent that the ratio $S/S''$ will always be less than 1 when $E_c<E_m$. However, it is known that grouted metal stems provide adequate rotatory stability; thus, it is another objective of the present invention to have the ratio $S/S''$ as high as possible and preferably greater that 1; i.e., the rotatory stiffness of the metal-composite system should be preferably at least as stiff as the all-metal system which is grouted in place with PMMA. To better define this criteria we consider the following typical values for the parameters defining the mechanical idealizations:

$D_o$=25 to 35 (mm) Bone outer diameter
$D_i$=12 to 22 (mm) Bone inner diameter and Composite stem and Press fit Metal stem diameter
$D_i=(D_i- 4)$ (mm) Grouted metal stem diameter
$L_1$=25 mm
$L_2$=60 mm
$L_3$=50 mm
$L_4$=75 mm
$E_b$=2.5 million psi
$E_m$=16 million psi for Ti-6Al-4V alloy
$E_p$=0.33 million psi The ratio $S/S''$ was computed as a function of composite modulus up to 16 million psi, the modulus of Ti alloy, for a 25 mm and 35 mm bone outer diameter respectively. For each stem diameter there is a modulus $E_2$ such that the ratio $S/S''$ is greater than 1 if $E_c$ is greater than $E_2$. We specify this criteria for the preferred lower limit on the modulus $E_c$ as:

$$E_c \geq E_2 \text{ where } S/S''=1 \text{ when } E_c=E_2$$

The computed values of $E_1$ and $E_2$ were plotted as a function of stem diameter. The most preferred embodiments of the current invention have composite moduli which fall between these two curves at the given stem diameter. It is apparent that all the values in this most preferred range fall in the range 1 to 8 million psi so this forms a preferred range for the invention.

It will be apparent to those skilled in the art that more exact mechanical idealizations, e.g., those using three dimensional finite element analysis, can be used to define the most preferred range for composite modulus even more exactly than in the approximate analysis disclosed above.

Ultimately, the fatigue strength of the composite distal stem will further constrain the exact details of the composite construction. Often, strength correlates positively with modulus; strength considerations may impose higher values for the composite modulus than specified in the preferred or most preferred range.

The region between the neck and distal stem, the proximal body, represents the most desirable region for load transfer to bone. Local modulus in this region could be optimized to direct load at the medial (inner) calcar region of the femur to avoid the stress protection and bone remodeling often seen there. In the simplest embodiment of the invention the modulus is made to vary continuously from that prescribed in the neck region to that prescribed in the distal stem region so as to avoid stress concentrations which might otherwise compromise device durability.

An orthopedic implant is disclosed, which is fabricated from composite materials such that the extraosseous portion has an equivalent flexural modulus greater than 8 million psi and preferably greater than 16 million psi and the second intraosseous portion has an equivalent flexural modulus of up to 16 million psi, more preferably in the range of 1 million to 8 million psi. The first intraosseous portion of the component has an equivalent flexural modulus intermediate between them and which preferably varies continuously.

The present orthopedic device may be fabricated by filament winding or braiding in which the modulus variation is accomplished by a continuous variation in the winding or braiding angle. A winding or braiding process which results in a constant angle along the axis is known as a linear winding or braiding process. A process which results in a changing angle along the axis is known as a nonlinear process.

Figure 2:
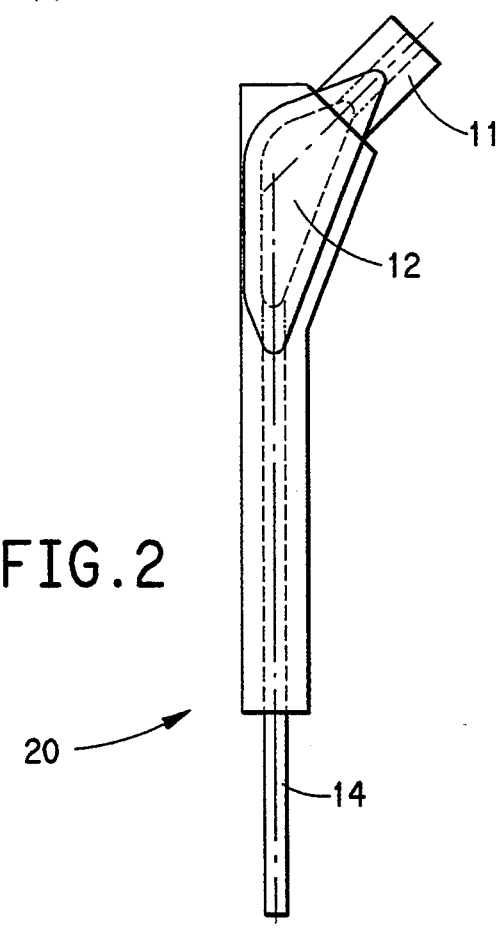
FIG. 2 is a side view of mandrel components useful to form an orthopedic implant according to the invention.
Figure 9A:
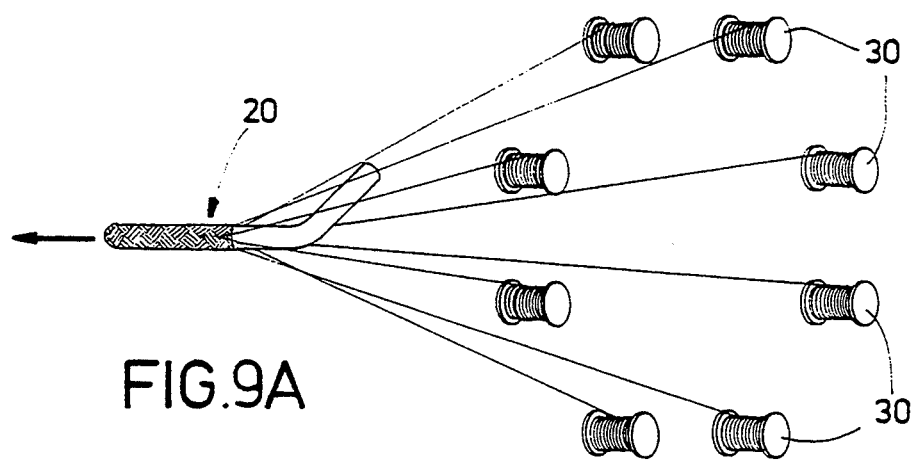
FIGS. 9A and 9B depict a mandrel being wound or braided and a possible fiber orientation for an implant according to the invention.
Figure 9B:
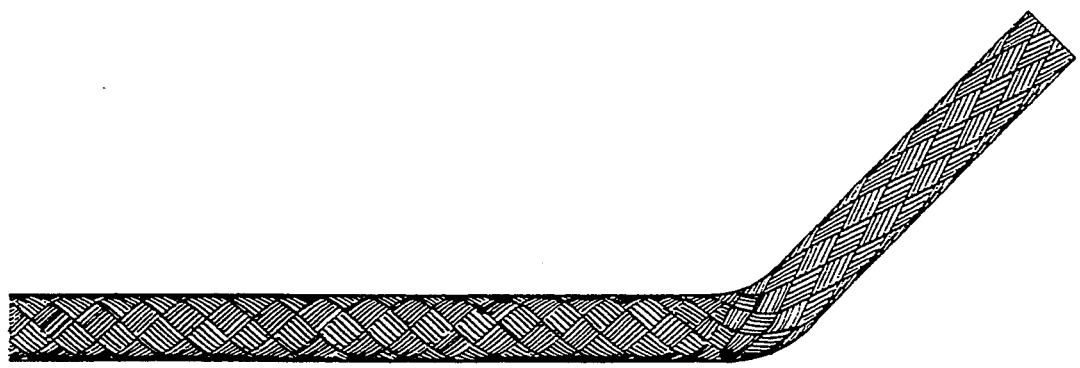

Devices according to this invention may be made by first fabricating a mandrel 20 such as in FIG. 2 or as in FIG. 9A bent to give an angle beta equal to the stem-neck angle desired in the finished part. This mandrel is fed into a braiding machine (such as manufactured by Mosberg Corporation) which applies bundles of reinforcing filaments at a prescribed orientation by controlling the rate of movement of the mandrel relative to the motion of the bobbins 30 feeding the filament bundles. The mandrel 20 is shown being fed into the braiding machine distal end first. As the mandrel advances such that the filament bundles are applied to the proximal region of the mandrel, the relative motion of the mandrel and bobbins is adjusted to reduce the angle which the filaments make with the mandrel axis, thus producing a higher modulus in this region. The resulting fiber orientation pattern after a single pass through the braiding machine is shown schematically in FIG. 9B. The part may pass through the braiding machine several times to apply a number of layers of filaments so as to produce a final part of the correct thickness. Fiber angles in each layer may be different from those in other layers. Furthermore, all layers need not run the full length of the mandrel. This allows variations in part thickness along the length.

Figure 10:
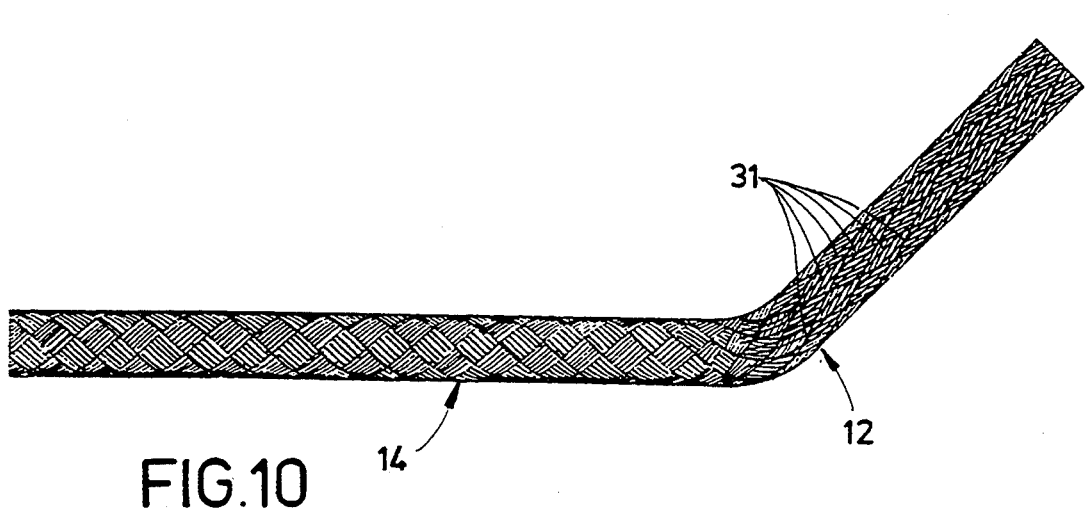
FIG. 10 depicts an implant according to the invention including axially oriented fibers.

The local modulus of the device may be further varied by introducing axially oriented fibers along all or a portion of the length of the device. These axially oriented fibers may comprise a reinforcing fiber which is the same as or different from the angled fibers. A braiding machine is configured to introduce axially oriented filaments among the angled braiding filaments fed from bobbins 30. FIG. 10 shows schematically a layer of axial fibers 31 applied by this process in which axially oriented fibers are incorporated in the proximal body 12 of the device, thus, increasing the modulus in only that region.

Filament bundles of varying orientation may also be applied using a filament winding machine instead of a braiding machine. Orientation of the filament bundles typically fed from a package is controlled in this process by the motion of a payout eye, through which filaments pass, relative to the rotation of a chuck which holds the mandrel. By increasing the speed of the payout eye relative to the chuck rotation, the fiber orientation angle is reduced as the proximal body of the mandrel is covered, thus, increasing its modulus relative to that in the distal stem. Note that curvature of a mandrel may be accomodated by moving the payout eye along a second axis normal to the first axis of motion so as to maintain close proximity of the payout eye and mandrel. The complex motion of the payout eye is best controlled by use of a computer. The motion of the filament bundle from a starting point on the mandrel to the end of travel along the mandrel and back to the starting point is called a circuit. One or more circuits is needed to complete a single layer of filaments. Furthermore, multiple layers of filaments may be needed to cover the entire surface of the part. The filament orientation within a layer and the extent of a layer along the mandrel length may vary from layer to layer.

The orthopedic device may hence be made of a plurality of layers composite material comprising filaments within a polymer matrix. These layers are independently arranged about the extraosseous portion and the first and second intraosseous portions. By "independent arrangement" it is meant that each layer may contain any filament type, laid down in any fashion (linear, nonlinear, wound, braided, containing axial windings or angular windings, and the like) and at any density, irrespective of other layers. It is further meant that the various portions of the device may contain different numbers of layers.

It is appreciated that there is an endless set of combinations of numbers of layers of composite with selected orientations of fibers. Without intending to limit the generality of the foregoing, a preferred device is a hip implant wherein the neck and proximal body contain layers of composite material with the filaments of each layer independently disposed at 5°–45° from the longitudinal axes of these regions, while the distal stem contains layers of composite material with the filaments of each layer independently disposed at 30°–90° from its longitudinal axis. By "independently disposed" it is meant that between layers and within each layer the fibers are laid down in any fashion and are of any type irrespective of other fibers. The neck and proximal body may contain an additional plurality of layers, with the filaments independently disposed at 0°–5° from their longitudinal axes.

Alternatively the filament bundles may be applied to the mandrel 20 by use of a robot. In particular, a robotic winding system such as that disclosed in U.S. Pat. No. 4,750,960 incorporated by reference herein is ideal for this application. In this system the mandrel remains stationary and the various degrees of freedom of the robot allow application of the filament bundles to the mandrel at any orientation. It is apparent that fiber orientation may be easily achieved with this technique. Furthermore, use of a robot facilitates large changes in orientation angle within a given winding circuit. In particular, orientation can be changed such that individual circuits have a typical helical geometry in the distal region of the structure and become axial in the proximal region.

Braiding or winding onto a curved mandrel makes removal of the entire mandrel difficult. It may be desirable to remove all or part of the mandrel to achieve specific mechanical or biocompatibility objectives. A multi part structure may be used to facilitate removal of one section of the mandrel, e.g., the distal section, while another section, e.g., the proximal section is captured in the finished part. For this purpose the mandrel is any number of parts joined so that all or some components can be removed.

In an alternative system filament bundles are wound about the distal stem in the normal helical manner. However, rather than winding around the proximal body of the mandrel they are laid upon a tool or plate configured to support the windings in the exterior shape of the proximal body. After winding the appropriate number of circuits to build up the desired part thickness, the mandrel part together with the plate may be removed leaving the all composite part. The robotic winding system disclosed in U.S. Pat. No. 4,750,960 is especially well suited for creating this type of structure. This structure may itself serve as a captive mandrel for further winding or braiding forming a sheath-core structure. This particular approach is especially useful for forming hip implants with complex outer geometry designed to match the normal anatomy of the intramedullary canal of the femur. In this case the core of the implant can be designed primarily to achieve the structural requirements of the device, including the intended variation in composite modulus along the length, while the sheath can be designed primarily to achieve the complex anatomical shape.

The sheath therefore forms an interior portion shaped substantially as the exterior surface of the core (which can be the distal stem and the proximal body, for example) and an exterior portion shaped substantially as the interior surface of the aperture into which it is inserted.

Those skilled in the art will recognize that the matrix of the composite may be introduced prior to braiding or winding by precoating the reinforcing filaments, during braiding or winding, or after braiding or winding by processes such as resin transfer molding. It is also noted that voids within the part and imperfections in the surface of the part may be corrected by finishing operations such as molding or autoclaving.

In an alternative embodiment according to the invention, a sheath/core structure is formed such that the core of the structure largely achieves the mechanical objectives of the device including the modulus variation and the sheath largely achieves the desired shape of the device.

The composite material may comprise wound filaments embedded in a polymer matrix. The filaments are selected from any of a wide variety of candidates, the criteria of selection being ease of manipulation, and compatibility with the polymer matrix. Preferred filaments include carbon, graphite, glass and aramid fiber. The organic matrix is selected according to its compatibility with both the wound filaments and the tissue and other materials with which it comes into contact. The matrix is preferably selected from polysulfone, polyether-ether-ketone, polyether-ketone-ketone, polyimide, epoxy and polycyanate.

The nature of the variable modulus and methods of making the orthopedic devices of the invention, will be readily understood by having reference to the examples that follow herein.

EXAMPLE

Example 1

A multilayer, circular braid of Kevlar 49 ® (a registered trademark of E. I. du Pont de Nemours and Company) tow was fabricated on a wire mandrel which was bent to give the curvature typical of the stem-neck angle of a hip implant. Three plies were first applied with a braid angle of 50° to 60° at all points along the length of the device. Four plies of braid with the same angle were then applied to the proximal region to build thickness. Finally, an additional four plies were braided along the entire length of the device such that the distal region of the stem had a braid angle of 50° to 60° while the proximal region had a-braid angle of 35°. An epoxy resin was applied to each ply after braiding. The entire part was cured as a unit after all layers were braided.

Examples 2

The braid was formed on a wire mandrel bent to the shape typical of the neck-stem geometry of a femoral hip component. Three plies of Kevlar 49 ® tow were braided along the entire length of the structure at a 50° to 60° angle with respect to the axis of the structure. Four additional plies of Kevlar 49 ® were braided in the proximal region of the structure to build up thickness. Two additional full length plies of Kevlar 49 ® were then applied. Finally, two plies were braided to generate the along-the-length modulus gradient. Specifically, 16 axially oriented graphite yarns ("pass through" yarns) were introduced amongst the 32 braiding yarns forming a triaxial braid in the proximal region of the device. The axial graphite yarns were cut as the braider moved into the distal region of the device, yielding a gradient stiffness structure. The polymer matrix was applied to each ply after braiding. The entire structure was cured after all plies were braided.

Example 3

A graphite/epoxy prepreg tow (graphite fibers pretreated with epoxy resin) was wound onto a shaped mandrel using a robot and computer controls. Wind angle was varied such that the distal region of the stem had a wind angle from 45° to 55° while the proximal region of the stem had a wind angle of 25° to 35°, thus, introducing a gradient in modulus such that the proximal region was stiffer than the distal region. The parts were cured in an oven at 350° F. after winding.

Example 4

Using a robotic winding system and a winding circuit including primarily nonlinear windings for the distal stem and primarily axial windings for the proximal body, a tow of graphite fiber precoated with a thermoplastic resin was wound into the shape of a hip implant. The thermoplastic coated tow was consolidated during winding by the application of elevated temperature and pressure created by tensioning the tow and by use of a heated shoe which presses the tow against the mandrel of previously wound fibers. Several layers of material were applied in this fashion to achieve the desired part thickness. Layers which included the helical/axial circuit were used as well as layers which were purely helical in geometry but with lower angle in the proximal region of the structure.

Example 5

Using a robotic winding system and tooling and winding circuits, the core of sheath/core hip implant structure was wound from graphite tow precoated with a thermoplastic matrix resin. The thermoplastic coated tow was consolidated during winding by the application of elevated temperature and pressure created by tensioning the tow and by use of a heated shoe which presses the tow against the mandrel or previously wound fibers.

After producing the core structure, additional helical windings were applied using the same robotic winding system in a manner which produced an outer shape of complex shape aimed at closely matching the anatomy of the medullary canal of the femur.

I claim:

1. A load bearing orthopedic device for human implantation comprising:
    an extraosseous portion;
    a fist intraosseous portion attached thereto; and
    a second intraosseous portion attached to said first intraosseous portion;

the orthopedic device having a length, a longitudinal axis, and modulus that varies continuously along the length therefore, and being made of composite material comprising, a plurality of filaments disposed within a polymer matrix which is compatible with said filaments, tissue and other materials with which it comes into contact with and further wherein said filaments are wound or braided in a varying angle with respect to the longitudinal axis resulting in continuous modulus variation along the entire length of the device.

2. The orthopedic device of claim 1 wherein the filaments are selected from the group consisting of carbon, graphite, glass and aramid fiber.

3. The orthopedic device of claim 1 wherein the polymer matrix is selected from the group consisting of polysulfone, polyether-ether-ketone, polyether-ketone-ketone, polyimide, epoxy and polycyanate.

4. The orthopedic device of claim 1 wherein said filaments are disposed in a helical pattern.

5. The orthopedic device of claim 1 wherein said filaments are disposed in a braided pattern.

6. The orthopedic device of claim 4 or 5 wherein the extraosseous portion and the first intraosseous portion each have a longitudinal axis, and filaments are further oriented axially along the longitudinal axes of the extraosseous portion and the first intraosseous portion.

7. An orthopedic device for human implantation comprising:
   an extraosseous portion;
   a first intraosseous portion attached thereto; and
   a second intraosseous portion attached to said first intraosseous portion;
   the orthopedic device having a length and being made of a plurality of layers of composite material said composite material comprising a plurality of filaments disposed within a polymer matrix which is compatible with said filaments, tissue and other materials with which it comes into contact with and said layers being independently arranged about extraosseous portion and the first and second portions, the first intraosseous portion, and the second intraosseous portion each having a modulus and a longitudinal axis, and each modulus decreases continuously along the entire length of the device from the modulus of the extraosseous portion to the modulus of the second intraosseous portion, and further wherein said filaments of each layer are wound or braided in a varying angle with respect to the longitudinal axis resulting in continuous modulus variation along the entire length of the device.

8. The orthopedic device of claim 7 wherein said filaments are disposed within the polymer matrix in a helical pattern or in a braided pattern.

9. The orthopedic device of claim 7 wherein the extraosseous portion and the first intraosseous portion each have a longitudinal axis, and said filaments further include tows oriented axially about the longitudinal axes of the extraosseous portion and the first intraosseous portion.

10. The orthopedic device of claim 7 useful as a human hip implant wherein said extraosseous portion is a neck adapted to engage a ball which rotatably engages a cup adapted to be attached to the pelvis, said first intraosseous portion is a proximal body, and said second intraosseous portion is a distal stem, the proximal body and the distal stem being adapted to be received within the femoral canal.

11. The orthopedic device of claim 10 wherein the neck and proximal body are comprised of a plurality of layers of said composite material wherein each layer includes filaments which are independently disposed at an angle of 5°–45° from the longitudinal axes thereof, and the distal stem is comprised of a plurality of layers of said composite material wherein each layer includes filaments which are independently disposed at an angle of 30°–90° from the longitudinal axis thereof.

12. The orthopedic device of claim 11 wherein the neck and proximal body additionally comprise a plurality of layers of said composite material wherein each layer includes filaments which are independently disposed at an angle of 0°–5° from the longitudinal axes thereof.

13. The orthopedic device of claim 11 wherein the distal stem, the proximal body or both comprise a core and a sheath, said sheath comprising a plurality of filaments disposed to form an interior portion shaped substantially as the exterior surface of the core and an exterior portion shaped substantially as the interior surface of the aperture within the femoral canal formed to accommodate the device.

* * * * *